(12) United States Patent
Vaccaro et al.

(10) Patent No.: US 7,752,882 B2
(45) Date of Patent: *Jul. 13, 2010

(54) POROSITY REFERENCE STANDARD UTILIZING A MESH

(75) Inventors: Christopher M. Vaccaro, Ofallon, MO (US); April L. Beisiegel, Freeburg, IL (US); Ron DeFonce, High Ridge, MO (US)

(73) Assignee: The Boeing Company, Chicago, IL (US)

( * ) Notice: Subject to any disclaimer, the term of this patent is extended or adjusted under 35 U.S.C. 154(b) by 988 days.

This patent is subject to a terminal disclaimer.

(21) Appl. No.: 11/281,116

(22) Filed: Nov. 17, 2005

(65) Prior Publication Data

US 2007/0107520 A1 May 17, 2007

(51) Int. Cl.
*G01N 29/30* (2006.01)
(52) U.S. Cl. .................................. 73/1.86; 73/1.82
(58) Field of Classification Search ............ 73/620, 73/1.03, 1.86, 599, 600, 627, 1.82; 204/192.11, 204/192.12, 298.02, 298.23, 298.07, 192.13, 204/191.13, 298.03, 292.27
See application file for complete search history.

(56) References Cited

U.S. PATENT DOCUMENTS

| | | | |
|---|---|---|---|
| 3,784,043 A | 1/1974 | Presnick | |
| 3,908,439 A | 9/1975 | Peiak, et al. | |
| 3,933,026 A | 1/1976 | Ham | |
| 4,156,123 A | 5/1979 | Fischer et al. | |
| 4,173,139 A * | 11/1979 | Conn | 73/1.84 |
| 4,266,154 A | 5/1981 | Marshall | |
| 4,393,987 A | 7/1983 | Anderson et al. | |
| 4,406,153 A * | 9/1983 | Ophir et al. | 73/1.86 |
| 4,445,360 A | 5/1984 | Treder, Jr. | |
| 4,466,270 A * | 8/1984 | Kimura et al. | 73/1.86 |
| 4,566,330 A | 1/1986 | Fujii et al. | |
| 4,660,419 A | 4/1987 | Derkacs | |
| 4,674,334 A | 6/1987 | Chimenti et al. | |

(Continued)

FOREIGN PATENT DOCUMENTS

DE 2814336 B1 5/1979

(Continued)

OTHER PUBLICATIONS

U.S. Appl. No. 11/090,553, filed Mar. 25, 2005, Christopher M. Vaccaro and David A. Lilienthal.

(Continued)

*Primary Examiner*—J M Saint Surin
(74) *Attorney, Agent, or Firm*—Klintworth & Rozenblat IP LLC (57) ABSTRACT

The invention relates to pseudo porosity standards, and methods for their manufacture and use, which substantially mimic the effect porosity has on ultrasonic sound as it passes through a composite laminate. An ultrasonic inspection reference standard for composite materials having porosity may include a member having at least one thickness and at least one mesh. The member may be manufactured from a fiber-free polymer resin using a stereo lithography process. Use of the mesh produces a standard which transmits ultrasonic energy, with the mesh scattering and attenuating the energy. The manufactured reference standard may replace more costly porous, fiber-reinforced, composite reference standards in the aircraft industry and in other non-aircraft applications.

19 Claims, 7 Drawing Sheets

U.S. PATENT DOCUMENTS

| | | | |
|---|---|---|---|
| 4,729,235 A | 3/1988 | Podlech | |
| 4,747,295 A | 5/1988 | Feist et al. | |
| 4,779,452 A | 10/1988 | Cohen-Tenoudji | |
| 5,054,310 A | 10/1991 | Flynn | |
| 5,065,520 A | 11/1991 | Shimizu | |
| RE33,789 E | 1/1992 | Stevenson | |
| 5,127,268 A | 7/1992 | Kline | |
| 5,163,027 A | 11/1992 | Miller et al. | |
| 5,163,077 A | 11/1992 | Dupre | |
| 5,196,343 A | 3/1993 | Zerhouni et al. | |
| 5,238,556 A | 8/1993 | Shirkhan | |
| 5,312,755 A | 5/1994 | Madsen et al. | |
| 5,525,385 A | 6/1996 | Weinstein et al. | |
| 5,551,881 A | 9/1996 | Henderson et al. | |
| 5,603,797 A * | 2/1997 | Thomas et al. | 156/272.8 |
| 5,637,175 A | 6/1997 | Feygin et al. | |
| 5,656,763 A | 8/1997 | Flax | |
| 5,662,566 A | 9/1997 | Marxrieser et al. | |
| 5,837,880 A | 11/1998 | Shakinovsky et al. | |
| 6,238,343 B1 | 5/2001 | Madsen et al. | |
| 6,364,986 B1 * | 4/2002 | Kieronski | 156/242 |
| 6,405,583 B1 | 6/2002 | Shirakawabe et al. | |
| 6,415,051 B1 * | 7/2002 | Callari et al. | 382/154 |
| 6,415,644 B1 | 7/2002 | Rockwood et al. | |
| 6,426,274 B1 | 7/2002 | Tayanaka | |
| 6,649,516 B2 | 11/2003 | Asakawa et al. | |
| 6,684,701 B2 * | 2/2004 | Dubois et al. | 73/579 |
| 6,803,095 B1 | 10/2004 | Halladay et al. | |
| 6,843,945 B1 | 1/2005 | Hsai-Yin Lee | |
| 6,925,145 B2 | 8/2005 | Batzinger | |
| 6,959,602 B2 | 11/2005 | Peterson et al. | |
| 6,962,701 B2 | 11/2005 | Koenig | |
| 6,962,739 B1 * | 11/2005 | Kim et al. | 428/47 |
| 7,010,980 B2 | 3/2006 | Meier | |
| 7,076,992 B2 | 7/2006 | Greelish | |
| 7,188,559 B1 | 3/2007 | Vecchio | |
| 7,216,544 B2 * | 5/2007 | Vaccaro et al. | 73/620 |
| 7,320,241 B2 | 1/2008 | Kollgaard et al. | |
| 7,353,709 B2 | 4/2008 | Kruger et al. | |
| 7,357,014 B2 | 4/2008 | Vaccaro et al. | |
| 7,418,860 B2 | 9/2008 | Austerlitz, et al. | |
| 7,424,818 B2 | 9/2008 | Vaccaro, et al. | |
| 7,509,832 B2 | 3/2009 | Vaccaro et al. | |
| 7,510,817 B2 | 3/2009 | Benoit et al. | |
| 2006/0213250 A1 * | 9/2006 | Vaccaro et al. | 73/1.86 |
| 2006/0234391 A1 | 10/2006 | Weiss et al. | |
| 2006/0265679 A1 * | 11/2006 | Scheffer et al. | 716/8 |
| 2007/0107520 A1 | 5/2007 | Vaccaro et al. | |
| 2007/0119256 A1 * | 5/2007 | Vaccaro et al. | 73/649 |
| 2007/0125177 A1 * | 6/2007 | Vaccaro et al. | 73/649 |
| 2008/0087093 A1 | 4/2008 | Engelbart et al. | |
| 2008/0134749 A1 | 6/2008 | Engelbart et al. | |
| 2008/0196475 A1 | 8/2008 | Engelbart et al. | |

FOREIGN PATENT DOCUMENTS

| | | |
|---|---|---|
| GB | 2221991 A | 2/1990 |
| JP | 61265565 | 11/1986 |
| JP | 08210953 A | 8/1996 |
| WO | 90/13024 A1 | 11/1990 |

OTHER PUBLICATIONS

Pending patent application, filed on Oct. 20, 2005 inventor Christopher M. Vaccaro, Ultrasonic Inspection Reference Standard for Porous Composite Materials (17 pages).

Pending patent application, filed on Oct. 20, 2005 inventor Christopher M. Vaccaro, Ultrasonic Inspection Reference Standard for Porous Composite Material (26 pages).

\* cited by examiner

| | |
|---|---|
| Form | Electroformed Wire Cloth |
| Square/Rectangle Size | 0.00442" (112 Microns) |
| Mesh Per Inch Range | Fine Mesh |
| Mesh Per Inch (Fine) | 200 x 200 |
| Percentage of Open Area Range | 70 - 79 |
| Percentage of Open Area | 78 |
| Wire Diameter | 0.00058" |
| Thickness | 0.002" |

FIG. 9

| | |
|---|---|
| Material Type | Plastic |
| Plastic Type | Nylon |
| Form | Woven Thermoplastic Mesh |
| Square/Rectangle size | 0.0012" |
| Mesh Per Inch Range | Fine Mesh |
| Mesh Per Inch (Fine) | 361 x 361 |
| Percentage of Open Area Range | 10 - 19 |
| Percentage of Open Area | 18 |
| Thread Diameter | 0.0016" |

POROSITY REFERENCE STANDARD UTILIZING A MESH

CROSS-REFERENCE TO RELATED APPLICATIONS

This application hereby incorporates by reference U.S. application Ser. No. 11/090,553, filed on Mar. 25, 2005, and titled Ultrasonic Inspection Reference Standard For Composite Materials.

BACKGROUND OF THE INVENTION

Composite laminate reference standards are employed when performing ultrasonic inspection on composite laminate materials. They are used to aid in the detection of planer defects such as delaminations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative planer conditions to aid in the detection of delaminations and foreign material. It is difficult however to tie detection and quantification of porosity to a representative planer defect reference standard without the introduction of defects that mimic porosity.

Due to this difficulty, one approach to detecting and quantifying porosity in composite laminates has been to build a set of porosity reference standards for a given material. This set of standards, which are costly to build and certify for use, are used to qualify production inspection systems and are used to determine the operating characteristics of ultrasonic inspection systems. The introduction of new composite materials and the cost associated with qualifying new and existing ultrasonic inspection systems to inspect those materials has produced a need to build and qualify less expensive porosity standards. The standards, once produced, can be tied back to material properties via effects-of-defects programs and used to evaluate the strength characteristics of the materials being inspected.

SUMMARY OF THE INVENTION

In one aspect of the present invention, an ultrasonic inspection reference standard for composite materials having porosity comprises a member having at least one thickness and at least one mesh. The member is manufactured from a fiber-free polymer resin.

In another aspect of the present invention, an ultrasonic inspection reference standard for composite materials having porosity comprises a member having at least one thickness and at least one mesh. The reference standard is adapted to contain at least one of the acceptable and rejectable ultrasonic properties of a fiber-reinforced composite part having porosity.

In a further aspect of the present invention, an ultrasonic inspection process for composite materials having porosity is provided. A reference standard is manufactured. The reference standard comprises a member having at least one thickness and at least one mesh. A fiber-reinforced composite part having porosity is inspected with an ultrasonic technique using the reference standard.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
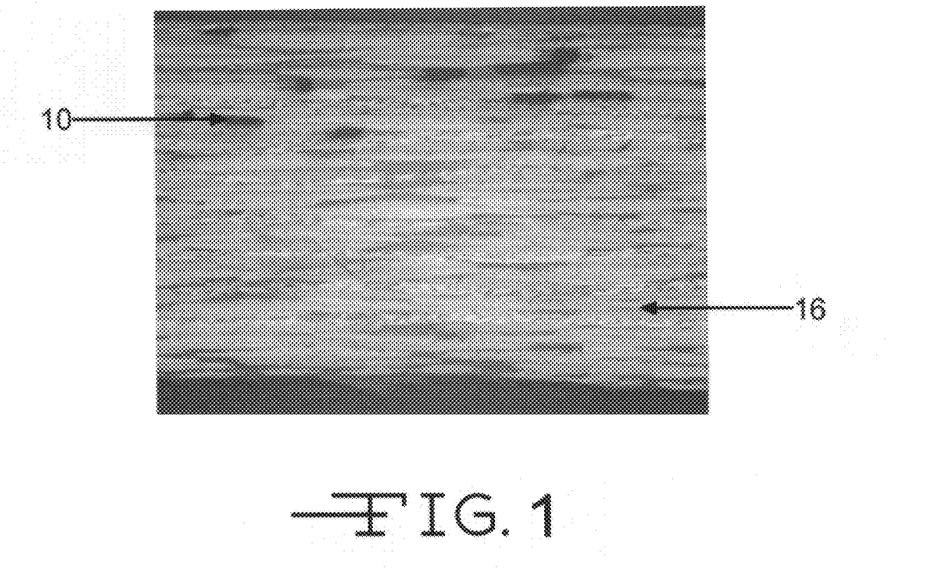
FIG. 1 is a photomicrograph of a composite laminate with porosity.
Figure 2:
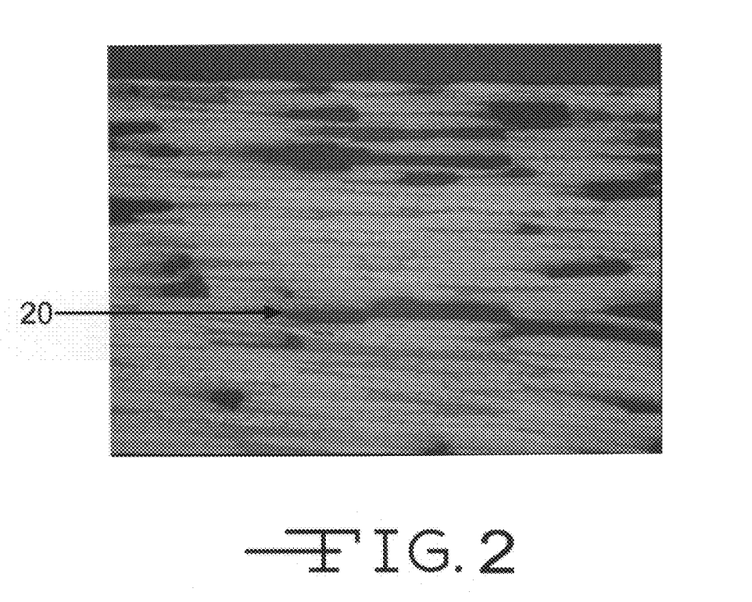
FIG. 2 is a photomicrograph of a composite laminate with large, planer-like porosity.

Composite laminates consist of two primary constituents including a fiber, and a resin matrix that bonds the fibers together. The fiber is typically graphite. Porosity in composite laminates is an unwanted product of the manufacturing cure cycle and is characterized by voids or a lack of resin within the laminate. FIG. 1 depicts a photomicrograph of a composite laminate with areas of porosity 10 shown as elliptical shapes that appear darker than the surrounding non-porous areas 16. The morphology and distribution of the porosity vary depending on a number of processing variables. The size of porosity also varies from relatively small diameters of 0.005" up to large planer conditions 20 like those illustrated in FIG. 2.

Figure 3:
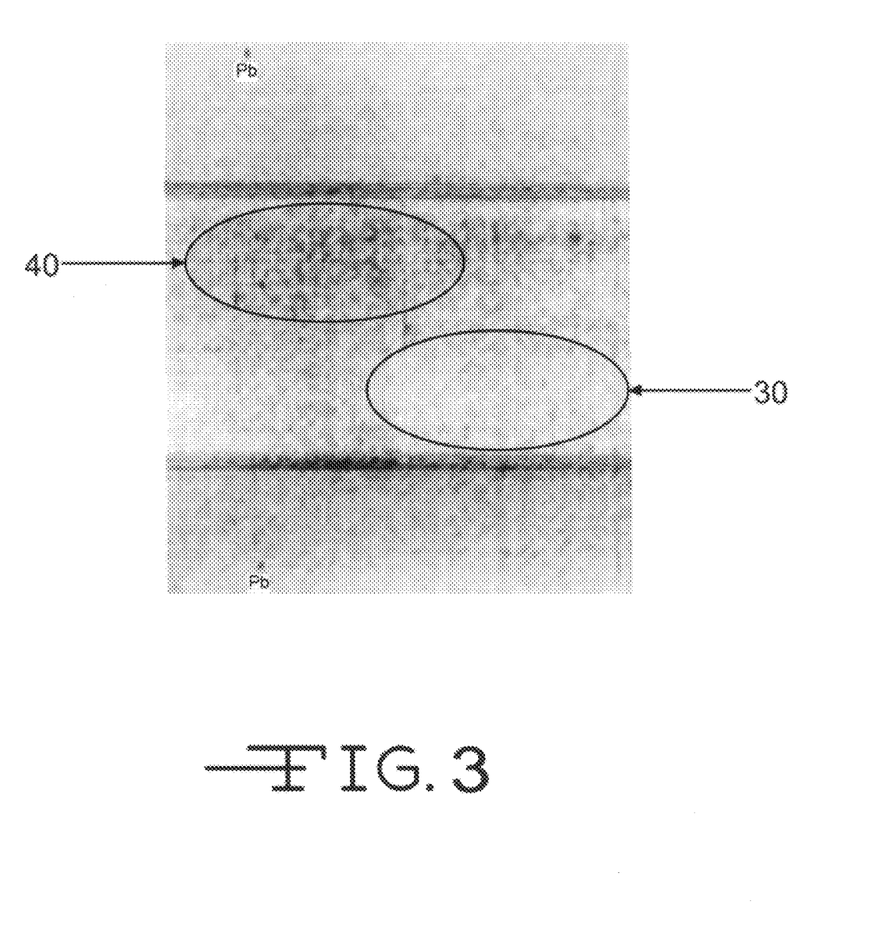
FIG. 3 is an ultrasonic C-scan of a composite laminate with porosity.

Porosity within a composite laminate may be quantitatively measured using high frequency ultrasonic methods. As the void content of a laminate increases, so does the ultrasonic attenuation. Ultrasonic attenuation is the combined loss of acoustic energy within the laminate which results from reflection and scattering of the sound pulse as it passes through the laminate. The ultrasonic C-scan in FIG. 3 illustrates this condition. The light gray areas 30 are where there is very little to no porosity in the laminate. The dark areas are where the laminate has porosity of some level.

Previous work has shown that photo-polymer resins used in stereo lithography (SLA), as well as conventional thermo set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference.

Figure 4:
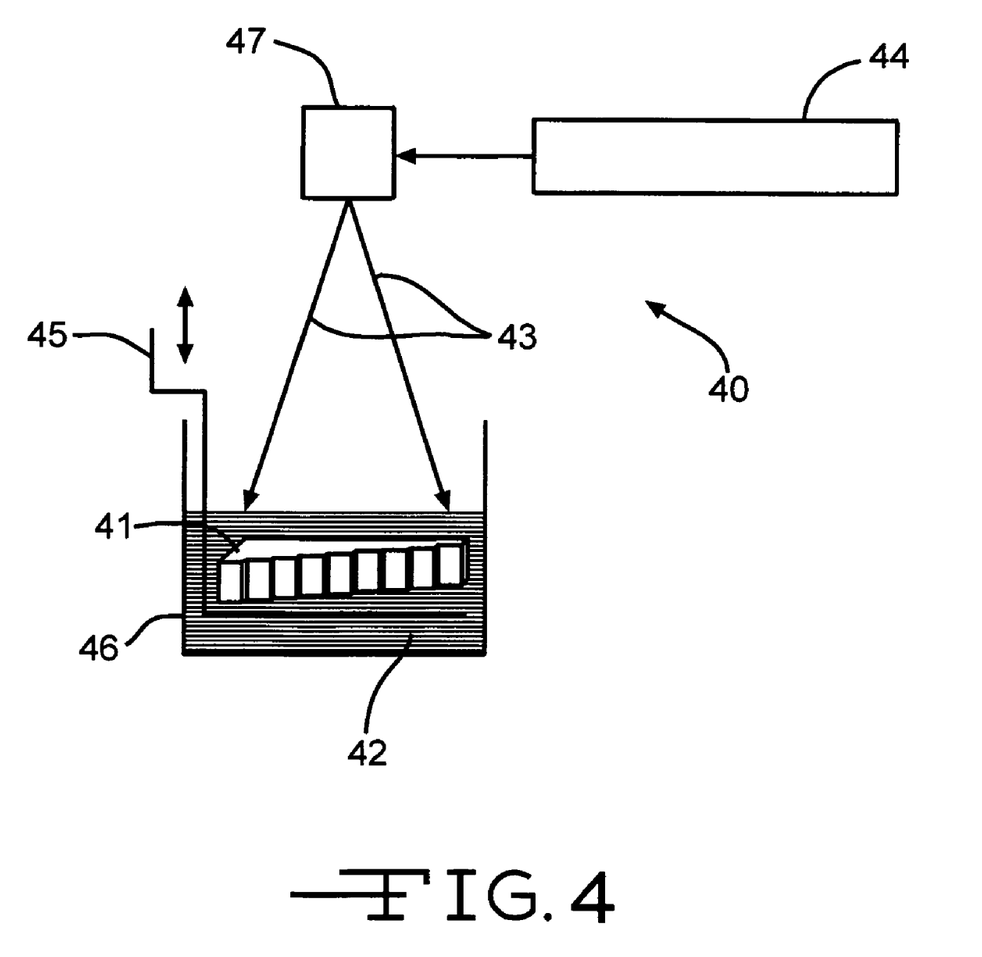
FIG. 4 is a front view of a stereo lithography process.

As shown in FIG. 4, the use of a stereo lithography process 40 may produce plastic parts 41, such as an ultrasonic inspection reference standard manufactured from a photo-polymer resin, directly from a 3D CAD (computer-aided design) model. The surface of a liquid photopolymer 42 is solidified layer-by-layer using a laser beam 43 emitted by a laser 44. When the laser beam 43 hits the liquid photopolymer 42, it solidifies the resin. When a layer is fully traced, a movable table 45 is then lowered in the vat 46 of resin. A scanner system 47 directs the laser beam 43 according to a loaded CAD model. The self-adhesive property of the material causes the layers to stick with each other and in this way a three-dimensional part 41 is formed in multi-layers. The stereo lithography process 40 is accurate and suitable for smooth surface finished parts. Parts manufactured using the stereo lithography process 40 may be used, for example, for conceptual designs, product verification, pattern making. The stereo lithography process 40 may be used, for example, for rapid prototyping. Use of the stereo lithography process 40 may enable the manufacture of ultrasonic inspection reference standards, such as a polymer resin reference standard, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured with the same physical steps as a prior art graphite-epoxy reference standard by using the stereo lithography process 40 shown in FIG. 4. Both standards were then ultrasonically scanned at 5.0 MHz using both the through-transmission technique and the pulse-echo technique. The obtained data for the through-transmission technique is illustrated in the x-y plot 50 of FIG. 5, while the obtained data for the pulse-echo technique is illustrated in the x-y plot 60 of FIG. 6. The plots demonstrate attenuation 52 and 62 measured in decibels (dB) versus thickness 51 and 61 measured in inches. The attenuation is a decrease in intensity of a sound wave as a result of absorption and scattering of ultrasonic energy. The plots 50 and 60 include data points 53 and 63 for a photo-polymer resin reference standard free of fibers, and data points 54 and 64 obtained for a prior art graphite-epoxy reference standard.

Figure 5:
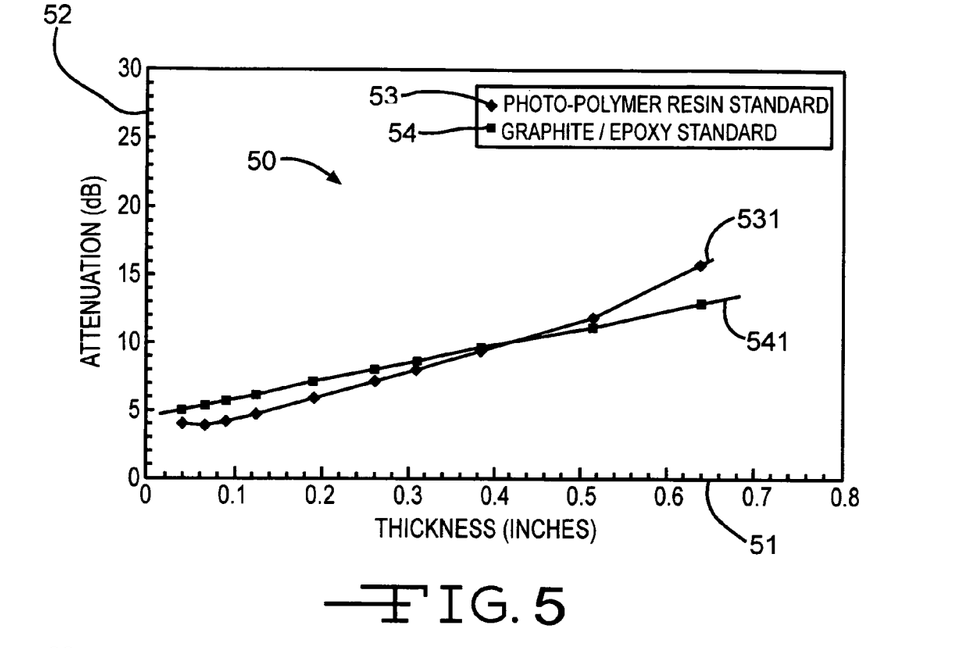
FIG. 5 is an x-y plot showing attenuation versus thickness applying through-transmission technique to both a photo-polymer resin standard and a graphite-epoxy standard.
Figure 6:
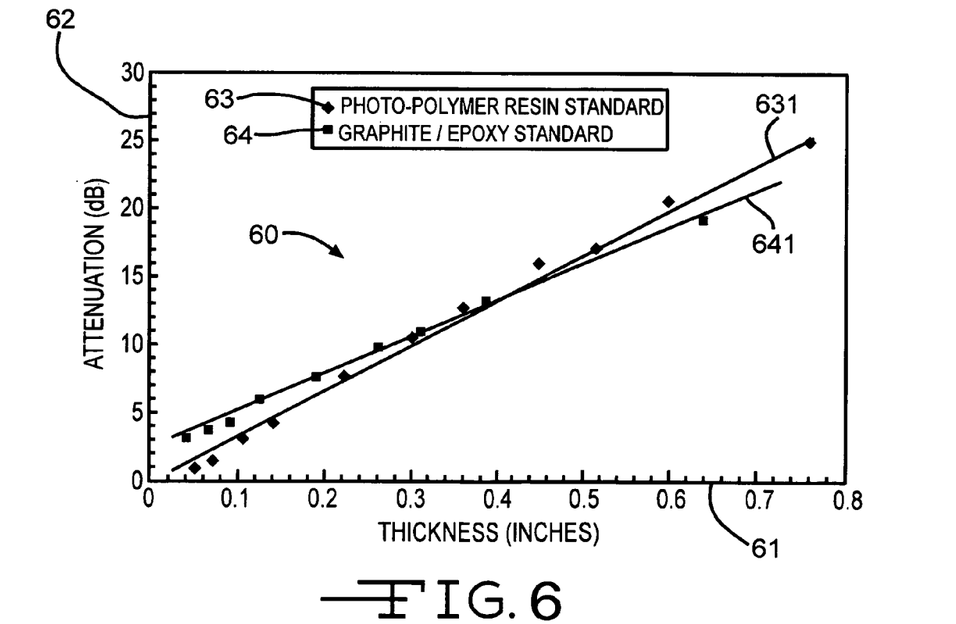
FIG. 6 is an x-y plot showing attenuation versus thickness applying pulse-echo technique to both a photo-polymer resin standard and a graphite-epoxy standard.

As shown in FIGS. 5 and 6, the slopes 531 and 631 of the photo-polymer resin standard is steeper than the slopes 541 and 641 of the prior art graphite-epoxy reference standard. However, the results are within the system noise, which is typically ±2 dB. Consequently, the prior art graphite-epoxy reference standard may be substituted with the photo-polymer resin reference standard that is fiber-free. Since ultrasonic attenuation is material dependent, altering the thickness of the polymer resin reference standard may be used to bring the slopes 531, 541, 631, and 641 in line if needed. Using this approach, a fiber-free polymer resin reference standard may be designed to have an equivalent thickness based on the material properties of the fiber-reinforced composite part to be tested and not the actual thickness of a prior art fiber-reinforced composite reference standard.

The present invention relates to pseudo porosity standards, and methods for their manufacture and use, which substantially mimic the effect porosity has on ultrasonic sound as it passes through a composite laminate. In a preferred embodiment of the invention, as discussed in more detail below, a pseudo porosity standard is manufactured using stereo lithography on a polymer resin to make a member having at least one thickness with similar acoustic properties of the composite laminate (fiber/resin combination). At least one mesh is incorporated into the member to produce a standard which transmits ultrasonic energy, with the mesh scattering and attenuating the energy. For purposes of this application, a mesh is defined as an interwoven weave of one or more materials having at least partial openings dispersed in the weave. The mesh may be made of one or more of wire, fiberglass, polymer, nylon, and a metallic material. In other embodiments, varying types of mesh may be used, and varying types of fiber-free polymer resin may be used, including the use of a polymer resin which is substantially similar to the resin of a composite material to be inspected. In still other embodiments, a non-stereo lithography process may be applied.

Figure 7:
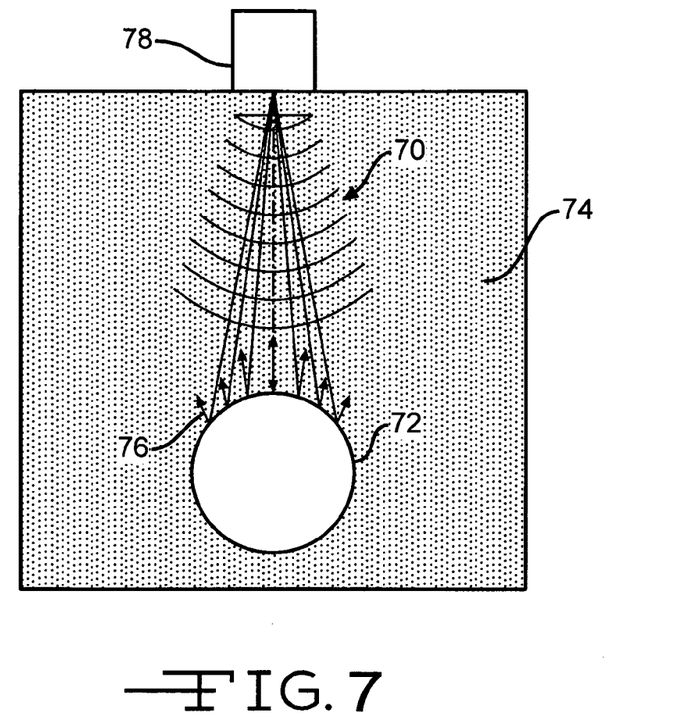
FIG. 7 is a simplified illustration of the ultrasonic two dimensional scattering which occurs off a circle.
Figure 8:
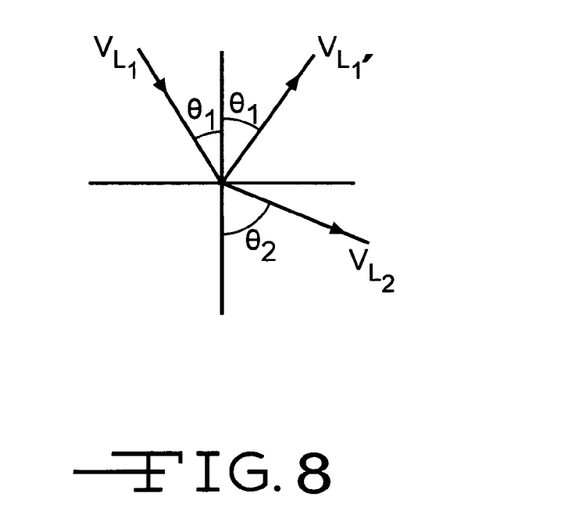
FIG. 8 depicts the principle of reflection and scattering under Snell's law.

The invention was arrived at in part due to the discovery that scattering of an ultrasonic pulse of energy can be produced through the placement of small voids within a homogenous median. This is the general principle for producing voids (porosity) within a composite laminate. Similarly, it was discovered that scattering can be accomplished through the introduction of hollow shafts in a homogenous median. The amount of ultrasonic scatter is dependent, in part, on the size of the shafts, the number of shafts and their proximity to one another. FIG. 7 is a simplified illustration of the ultrasonic two dimensional scattering 70 which occurs off a circle 72. In this example, the acoustic impedance mismatch between the base material 74, in this case a homogenous median, and the hollow circle 72, is large. This produces nearly 100 percent reflection 76 of the incident ultrasonic ray perpendicular to the ultrasonic transducer 78. As shown in FIG. 8, the principle of reflection and subsequent scattering is based on Snell's law as follows:

$$\frac{\sin\theta_1}{V_{L_1}} = \frac{\sin\theta_2}{V_{L_2}}$$

Snell's law provides the well-known relationship between angles of incidence and refraction for a wave impinging on an interface between two media with different indices of refraction. The law follows from the boundary condition that a wave be continuous across a boundary, which requires that the phase of the wave be constant on any given plane, resulting in $n_1 \sin\theta_1 = n_2 \sin\theta_2$, where $\theta_1$ and $\theta_2$ are the angles from the normal of the incident and refracted waves, respectively.

This same principle of scattering off a hollow shaft in two dimensions can be extrapolated to ultrasonic scattering off a mesh which produces three dimensional scattering. Generally, porosity produced in composite laminates is either discrete or takes on columnar shapes. Since graphite epoxy laminates consist of isotropic plies (0, 90, +45 and −45 degree plies) columnar voids can occur in any direction. Using a mesh, ultrasonic attenuation can be produced. The mesh, which mimics columnar porosity, is comprised of numerous arcs for the ultrasonic energy to scatter from which may result in scattering similar to that shown in the example of FIG. 7.

Figure 9:
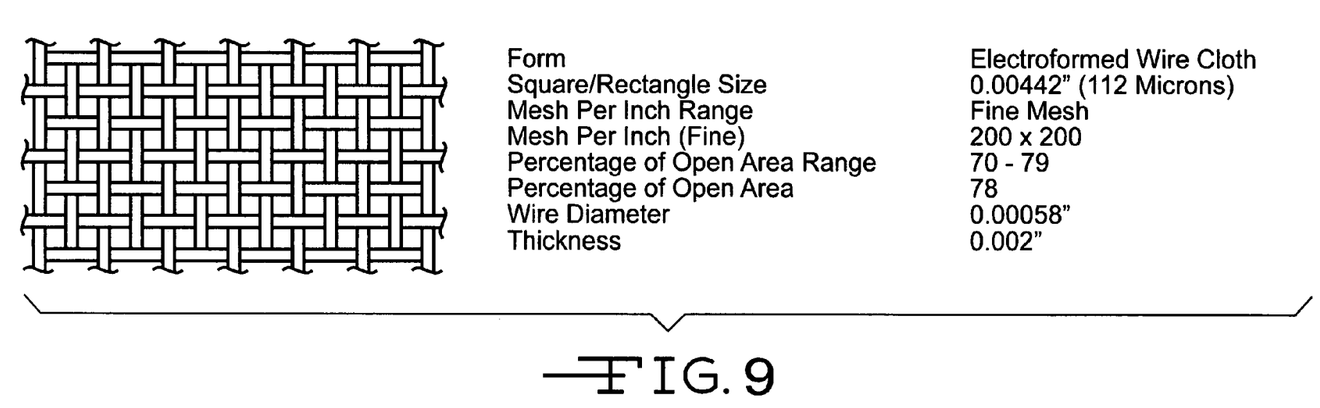
FIG. 9 is a woven mesh perform that may be incorporated into the present invention.
Figure 10:
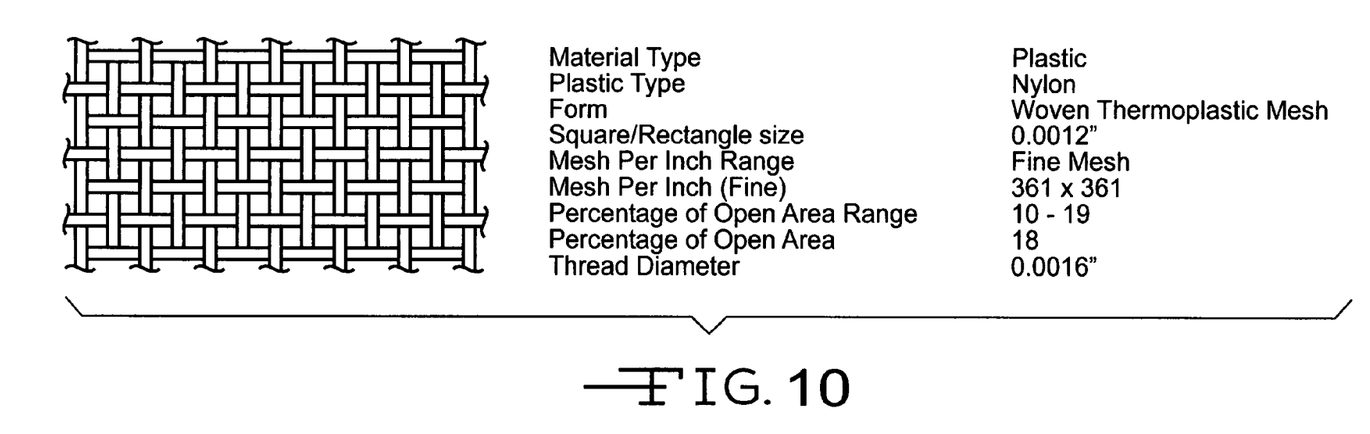
FIG. 10 is an example of another woven mesh perform that may be incorporated into the present invention.

The mesh may be of any size or material. Preferably, the mesh utilizes circumferential shapes to produce the desired scattering. FIGS. 9 and 10 depict examples of commercially available woven mesh performs that may be utilized. Each perform has unique acoustic properties based on a number of variables including the mesh's diameter, mesh range, percentage of open area and material type.

Figure 11:
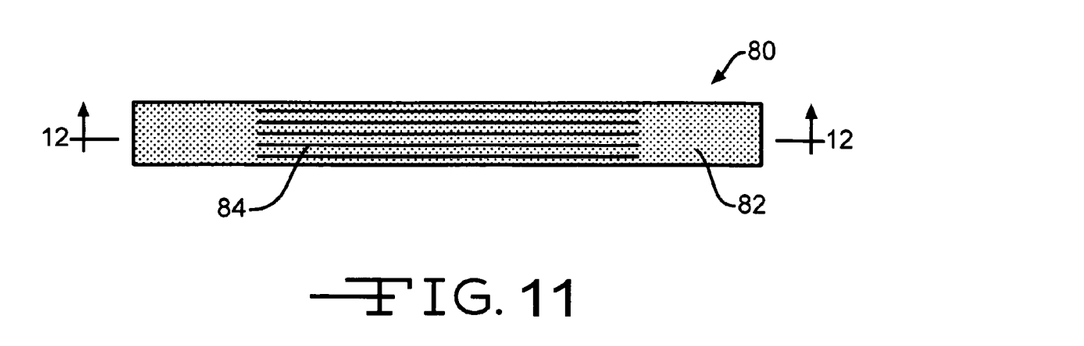
FIG. 11 is a side view of one embodiment of a reference standard under the present invention.
Figure 12:
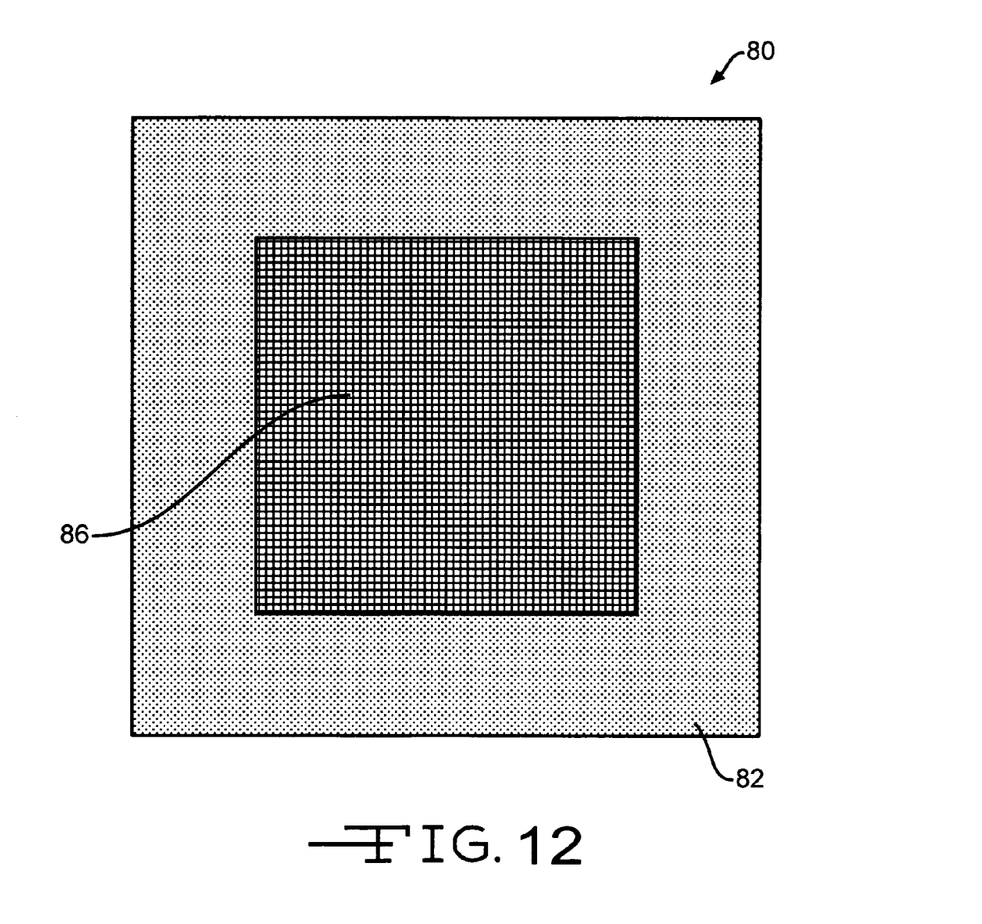
FIG. 12 is a partial cross-sectional view taken along line 12-12 of the embodiment of the present invention shown in FIG. 11.

To make the mesh useable as a scatting device, the mesh may be molded or inserted into a median that has similar acoustic properties of graphite epoxy. This may be accomplished by manufacturing a member out of a photopolymer resin using the SLA process. Narrow slots, comprising openings or holes, of uncured resin may be produced in the member during the SLA process. The width of the slots may approach the diameter or thickness of the mesh perform chosen for the application. In other embodiments, the slots may comprise varying sizes, orientations, and configurations. The mesh may be inserted into the uncured resin slots produced during the SLA process. The member may then be subjected to a final ultraviolet cure to advance the cure of the pre-cured resin as well as to cure the uncured resin around the mesh to secure it in place. At least one of the mesh diameter, location, mesh range, percentage of open area, material, spacing, and type may be chosen to achieve equivalent ultrasonic attenuation of porosity for a graphite epoxy composite laminate. FIGS. 11 and 12 illustrate side and cross-sectional views of a prototype standard 80 manufactured by utilizing the SLA process on a photopolymer resin to produce a member 82 having slots 84 within which meshes 86 are inserted.

In one embodiment of the invention, an ultrasonic inspection process starts with designing and building a three-dimensional model of the standard, according to a porous, fiber-reinforced composite part to be inspected. The porous, fiber-reinforced composite part to be inspected may comprise a graphite epoxy composite material having porosity. The three-dimensional model is designed to include at least one slot to accommodate at least one mesh at one or more locations where the resin will be uncured. At least one of the number, configuration, spacing, type, and size of the at least one slot, and/or at least one of the type, size, location, diameter, mesh range, percentage of open area, and spacing of the at least one mesh may be predetermined prior to manufacture of the standard in order to provide the standard with at least one of the acceptable and rejectable ultrasonic properties of the porous composite part to be inspected. In such manner, the designed reference standard may comprise substantially the ultrasonic properties of a fiber-reinforced composite reference standard. The at least one slot may be designed to be located in a variety of locations on or within the model. At other non-slot locations, the model may be designed to have solid surfaces where the resin will be cured using the SLA process. The model, which may be arrived at using computer-aided-drafting, is loaded into a stereo lithography machine to manufacture the reference standard by curing a photopolymer resin with a laser. In other embodiments, varying types of resins, such as a fiber-free polymer resin, and varying types of processes may be used to manufacture the standard.

In curing the photopolymer resin, the laser rasters back and forth curing resin only in the areas where the model indicates material to be. The areas to be slotted, as designated by the model, are not cured by the laser during the SLA process. The SLA process results in a member having at least one thickness. The member may comprise any shape, configuration, or thickness. The thickness of the member may be a substantially equivalent thickness based on the material properties of the composite material to be inspected. As the member is being built up during the SLA process, the at least one slot of uncured resin at the designated areas of the member are formed in accordance with the positioning of the slots of the model. After the areas around the at least one slot are formed in the member, at least one mesh is inserted into the at least one slot to allow the uncured resin to flow around the mesh. The at least one slot may be located in a variety of locations against or within the member. The SLA process is continued to encase the at least one mesh in place against or within the member. When the SLA process is finished, the standard is given a post UV cure to harden the resin and complete manufacture of the standard.

The process produces an ultrasonic reference standard, made of a fiber-free polymer resin member containing at least one mesh. The manufactured standard substantially mimics the ultrasonic properties of a porous composite material, allowing the replacement of fiber-reinforced composite reference standards. A varying amount of attenuation, or porosity, may be produced in the standard to accomplish the desired ultrasonic reference standard.

The manufactured standard may be used to inspect a fiber-reinforced composite part having porosity with an ultrasonic technique. For instance, the manufactured standard may be ultrasonically scanned using ultrasonic inspection, such as pulse-echo and through-transmission. Next, a porous, fiber-reinforced composite part may be ultrasonically scanned using the same technique. The data obtained from scanning the porous, fiber-reinforced composite part may be compared with the data obtained from scanning the manufactured standard. Based on the data, a decision may be made as to whether to accept or reject the composite part.

By using the combination of a fiber-free polymer resin member and at least one mesh in manufacturing the ultrasonic inspection reference standard, the reference standard may be manufactured at lower manufacturing cost, and in less time, using a method that does not require any tooling, as compared to many existing fiber-reinforced composite reference standards. The manufactured ultrasonic inspection reference standard may substantially comprise the ultrasonic properties of a graphite-epoxy reference standard or other type of reference standard made of varying materials. In such manner, the manufactured ultrasonic inspection reference standard may replace a graphite-epoxy reference standard, or other type of fiber-reinforced reference standard.

Using stereo lithography to produce slots adapted to contain at least one pre-determined mesh in a solid median member is of value because manufacturing costs may be roughly ten percent of the traditional cost of manufacturing composite standards with similar porosity. The ability to produce slots adapted to receive pre-determined mesh in particular patterns to mimic naturally occurring conditions makes this approach desirable in the manufacturing of pseudo porosity standards. Additionally, the nature of the manufacturing process, including its tailorability and repeatability, may enable the production of multiple reference standards having substantially equivalent acoustic properties to allow inspection of porous, composite parts around the world. The cost of manufacturing and certification of prior art reference standards may be limited by utilizing the present invention. The process may become the foundation for the development of pseudo porosity standards to characterize ultrasonic equipment, and may replace current composite reference standards, such as graphite-epoxy reference standards. The invention may be used for ultrasonic inspection of porous, composite parts used in the aircraft airframe industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials having porosity limitations, comprising:

(1) a member having at least one thickness, wherein said member is manufactured from a fiber-free photo-polymer resin using a stereo lithography process; and (2) at least one mesh, wherein said at least one mesh is disposed at least one of against and within said member in order to scatter ultrasonic energy, and wherein at least one or more of the type, location, diameter, mesh range, percentage of open area, and spacing of said at least one mesh is selected to produce a desired ultrasonic attenuation to mimic a specific porosity in the composite materials and to provide said ultrasonic inspection reference standard with at least one of an acceptable and resectable ultrasonic properties of said composite materials having porosity limitations.

2. The ultrasonic inspection reference standard of claim 1, wherein said fiber-free photo-polymer resin is substantially similar to the resin of the composite materials, having porosity limitations, to be inspected.

3. The ultrasonic inspection reference standard of claim 1, wherein said member comprises more than one thickness.

4. The ultrasonic inspection reference standard of claim 1, wherein said member is created using a 3D computer-aided-design model.

5. The ultrasonic inspection reference standard of claim 1, wherein said at least one thickness of said member is an equivalent thickness based on material properties of said composite materials, having porosity limitations, to be inspected.

6. The ultrasonic inspection reference standard of claim 1, wherein said at least one mesh is made of at least one of wire, fiberglass, polymer, nylon, and a metallic material.

7. The ultrasonic inspection reference standard of claim 1, wherein said member is manufactured using a method that does not require any tooling.

8. The ultrasonic inspection reference standard of claim 1, wherein said ultrasonic inspection reference standard is for graphite epoxy composite materials having porosity limitations.

9. The ultrasonic inspection reference standard of claim 1, wherein said member is defined by at least one slot in which said at least one mesh is positioned.

10. The ultrasonic inspection reference standard of claim 9, wherein said at least one slot is disposed within said member.

11. The ultrasonic inspection reference standard of claim 1, wherein each of the type, the location, the diameter, the mesh range, the percentage of the open area, and the spacing of the at least one mesh is selected to provide said ultrasonic inspection reference standard with at least one of the acceptable and rejectable ultrasonic properties of said composite materials having porosity limitations.

12. The ultrasonic inspection reference standard of claim 1, wherein said ultrasonic inspection reference standard is used to inspect a fiber-reinforced composite part of an aircraft structure.

13. An ultrasonic inspection process for composite materials having porosity limitations, comprising the steps of:

selecting one or more characteristics of the type, location, diameter, mesh range, percentage of open area, and spacing of at least one mesh to be disposed against or within a member having at least one thickness, in order to create a desired ultrasonic attenuation to mimic a specific porosity in the composite materials and to provide at least one of an acceptable and rejectable ultrasonic properties of said composite materials having porosity limitations:

manufacturing an ultrasonic inspection reference standard, having the one or more selected characteristics, by disposing the at least one mesh against or within the member having the at least one thickness using a stereo lithography process to make the member of a fiber-free photopolymer resin; and inspecting a fiber-reinforced composite part having porosity limitations with an ultrasonic technique using said manufactured ultrasonic inspection reference standard by: (1) ultrasonically scanning said manufactured ultrasonic inspection reference standard using an ultrasonic inspection technique to scatter ultrasonic energy off the at least one mesh in order to produce the desired ultrasonic attenuation; (2) ultrasonically scanning said fiber-reinforced composite part having porosity limitations using said ultrasonic inspection technique; (3) comparing data obtained from scanning said fiber-reinforced composite part having porosity limitations with data obtained from scanning said manufactured ultrasonic inspection reference standard; and (4) deciding whether to accept or reject said fiber-reinforced composite part having porosity limitations based on said data.

14. The ultrasonic inspection process of claim 13, further comprising manufacturing at least one slot in said member and disposing said at least one mesh in said at least one slot.

15. The ultrasonic inspection process of claim 13, wherein said at least one mesh is made of at least one of wire, fiberglass, polymer, nylon, and a metallic material.

16. The ultrasonic inspection process of claim 13, wherein the one or more selected characteristics comprise each of the type, the location, the diameter, the mesh range, the percentage of the open area, and the spacing of the at least one mesh.

17. The ultrasonic inspection process of claim 13, further comprising creating a 3D CAD model of the ultrasonic inspection reference standard prior to manufacturing the ultrasonic inspection reference standard.

18. The ultrasonic inspection process of claim 13, further comprising using the ultrasonic technique selected from the group consisting of pulse-echo technique and through-transmission technique to scan the ultrasonic inspection reference standard and to scan said fiber-reinforced composite part having porosity limitations.

19. The ultrasonic inspection process of claim 13, further comprising replacing a fiber-reinforced composite reference standard having porosity limitations with said manufactured ultrasonic inspection reference standard.

* * * * *